United States Patent [19]
Smernoff

[11] Patent Number: 4,600,697
[45] Date of Patent: Jul. 15, 1986

[54] APPARATUS AND PROCESS FOR EQUILIBRATING GAS AND LIQUID

[75] Inventor: Ronald B. Smernoff, Belmont, Calif.

[73] Assignee: Analytical Products, Inc., Belmont, Calif.

[21] Appl. No.: 697,269

[22] Filed: Jun. 17, 1976

[51] Int. Cl.[4] .................. G01N 33/50; G01N 1/00; B01L 11/00

[52] U.S. Cl. .................... 436/174; 55/68; 261/82; 422/50; 422/68; 422/81; 422/99; 422/101; 422/102; 422/104; 436/134; 436/138; 436/11; 436/68; 436/178

[58] Field of Search ............... 23/259, 253 R, 232 R, 23/254 R, 230 B, 258.5; 55/68; 422/50, 68, 81, 99, 101, 44; 436/11, 68, 174, 178; 261/82

[56] References Cited

U.S. PATENT DOCUMENTS 3,127,254 3/1964 Astrup et al. .................... 55/68
3,973,915 8/1976 Raffaele et al. .................. 23/259

OTHER PUBLICATIONS

Noonan et al., Clinical Chem., vol. 20, No. 6, 1974, pp. 660–665.

Primary Examiner—Michael S. Marcus
Attorney, Agent, or Firm—Fliesler, Dubb, Meyer & Lovejoy

[57] ABSTRACT

The invention is concerned with apparatus for equilibrating an aqueous solution with gas. The apparatus includes a gas vessel having therewithin a gas of a selectable composition at a pressure above ambient atmospheric pressure. Flow control means receive flow from the vessel and control a flow rate therefrom. A solution tube is provided having an aqueous solution therewithin. Conduit means lead from the flow control means to the tube below a liquid level of the aqueous solution. Means are also provided for causing the gas to be delivered within the aqueous solution below the liquid level as a plurality of bubbles. The process of the present invention is directed at simultaneously equilibrating a plurality of aqueous solutions each with one of a plurality of gas compositions. The process comprises positioning a plurality of solutions tubes, each having an open end and a closed end, in mating fit within a respective one of a plurality of cavities formed within a heat conductive block with the open ends of the tubes upwardly and a respective one of a plurality of aqueous solutions in each of the tubes. The temperature of each of the solutions is adjusted to be substantially equal by controlling the temperature of the block to a desired value. A respective one of the plurality of gas compositions is delivered below a respective liquid level of a respective aqueous solution within each respective one of the tubes in the form of bubbles.

23 Claims, 15 Drawing Figures

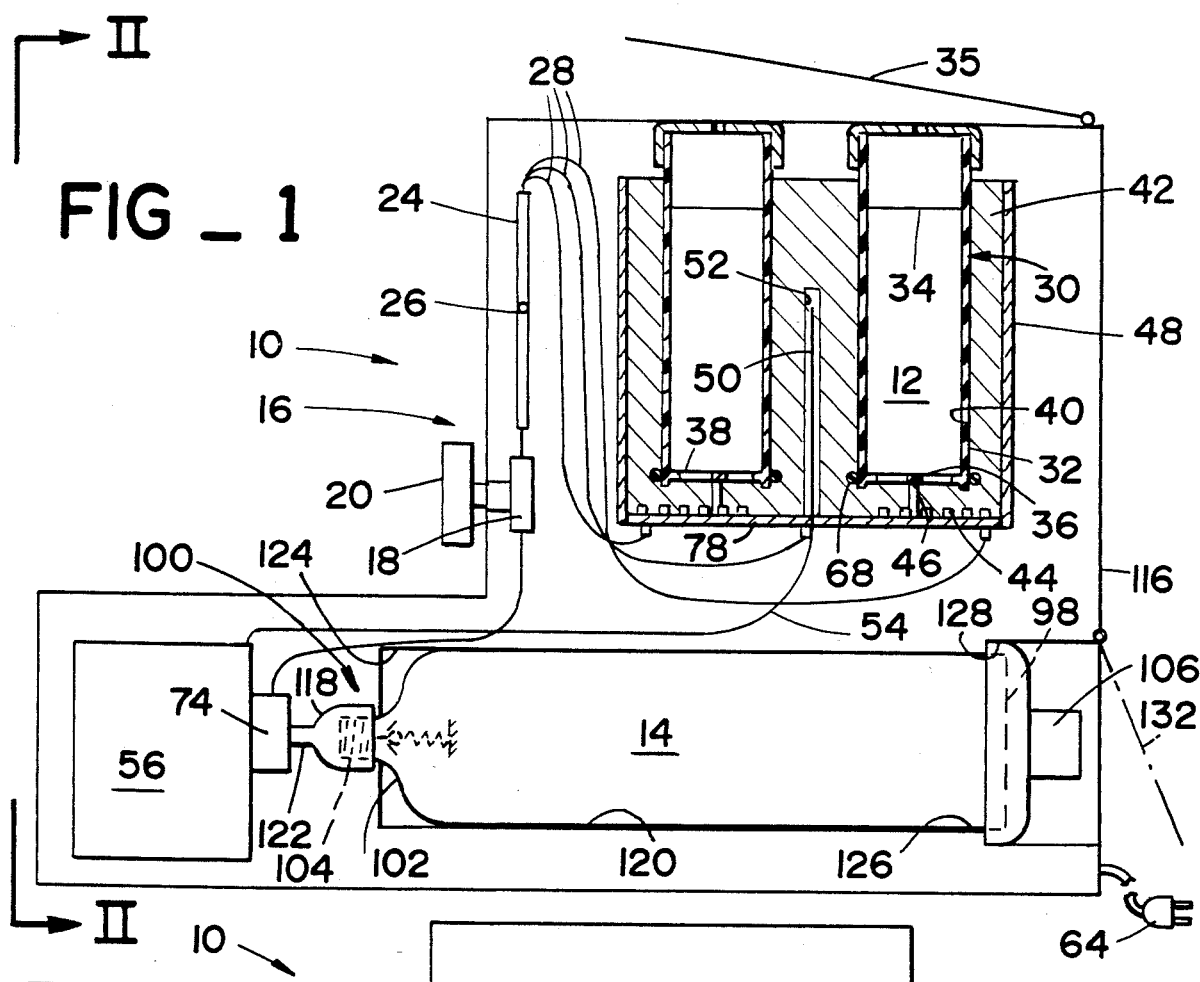
FIG _ 1
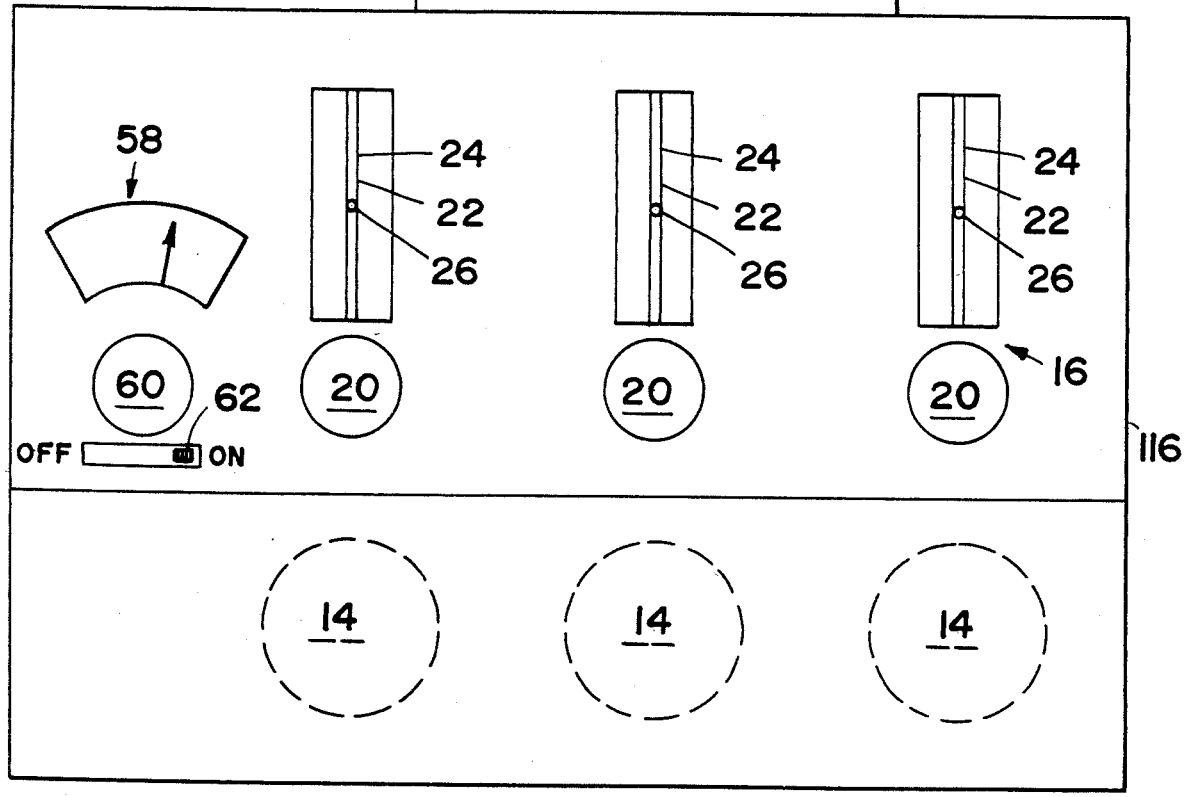
FIG _ 2

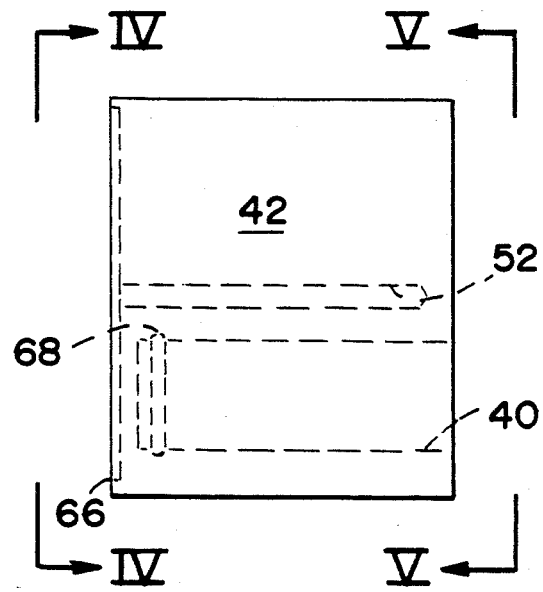
FIG _ 3
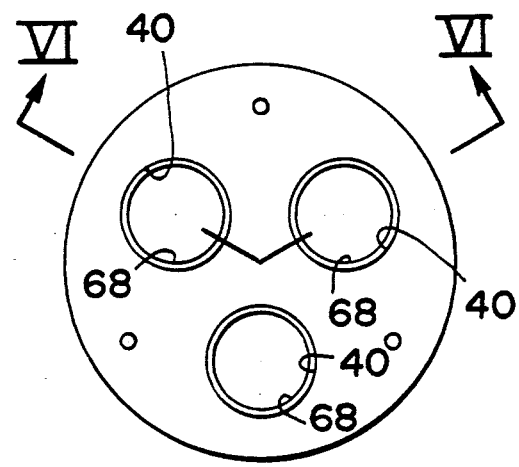
FIG _ 5
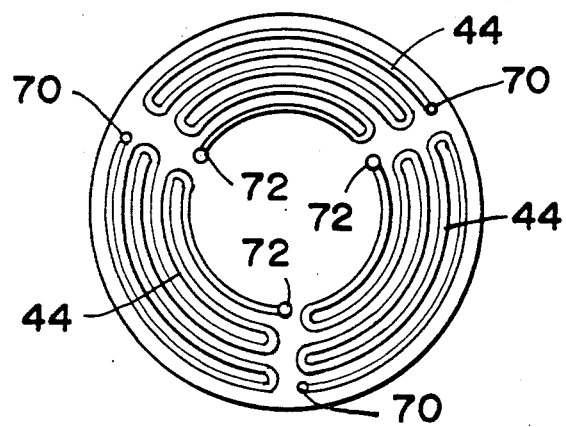
FIG _ 4
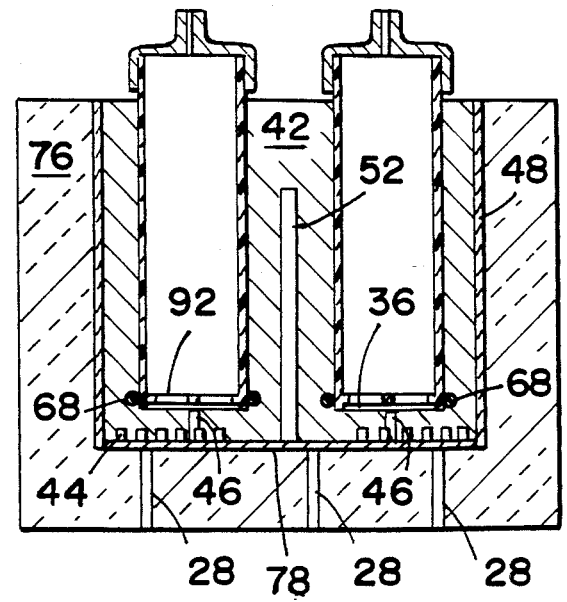
FIG _ 6
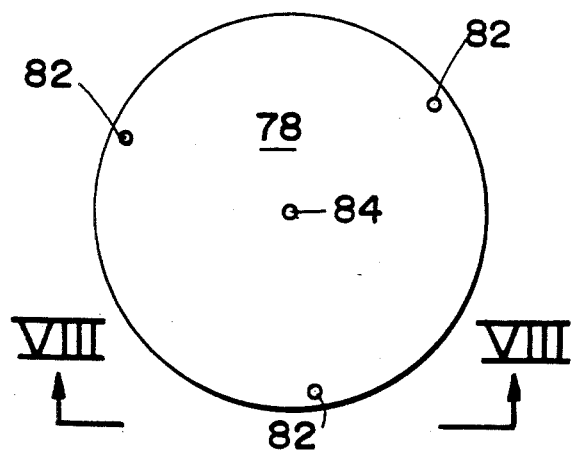
FIG _ 7
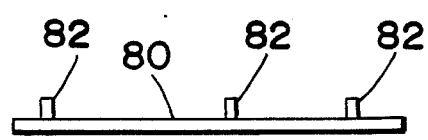
FIG _ 8

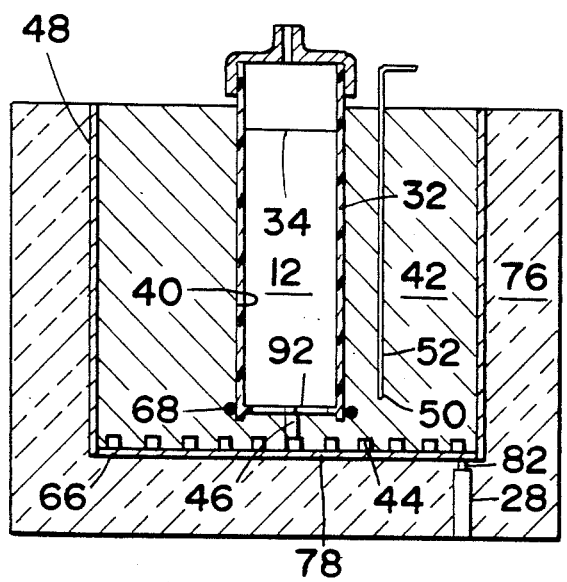
FIG_9
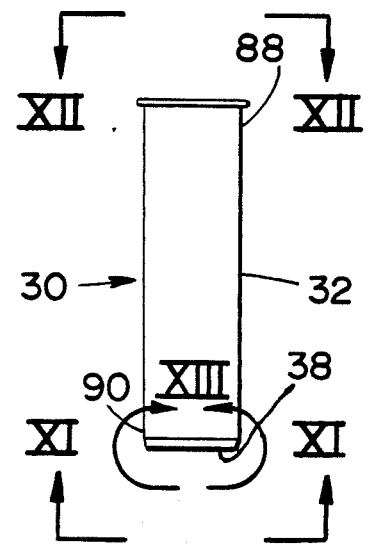
FIG_10
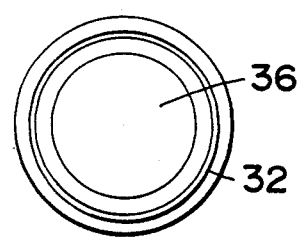
FIG_11
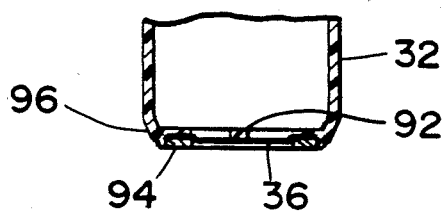
FIG_13
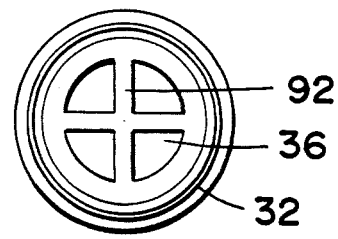
FIG_12
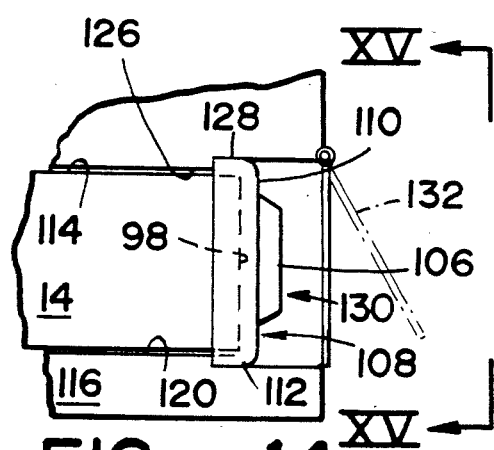
FIG_14
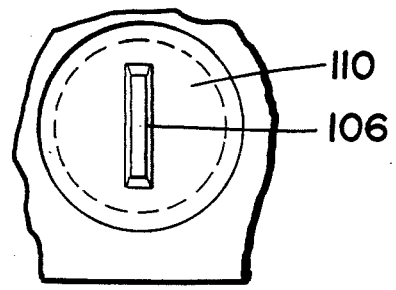
FIG_15

APPARATUS AND PROCESS FOR EQUILIBRATING GAS AND LIQUID

BACKGROUND OF THE INVENTION

1. Field of the Invention

The invention is concerned with an apparatus and process for equilibrating a hydrophilic liquid such as an aqueous solution with gas. More particularly the invention is concerned with such an apparatus for equilibrating standard solutions for preparation of standards useful in the determination of oxyhemoglobin dissociation curves and $P_{50}$ (value of $P_{O_2}$ at which the hemoglobin is 50% saturated) determinations.

2. Prior Art

Generally, determinations of oxyhemoglobin dissociation curves, $P_{50}$ determinations and the like are carried out on blood samples by analyzing the gases dissolved in the samples using an electrochemical blood gas analyzer.

In order to assure that the analyses of the dissolved gas in the blood samples are accurate the blood gas sample analyzer is generally calibrated against a standard solution made by contacting an aqueous solution with a gas sample of known concentration of for example oxygen, carbon dioxide and nitrogen. The instrument is then checked against two other samples of aqueous solutions which have been each equilibrated with other known mixtures of oxygen, carbon dioxide and nitrogen. Hence, while the instrument is calibrated against a single sample its accuracy is checked against usually two other known samples to assure that the instrument is operating properly.

A large percentage of medical laboratories which regularly analyze blood samples for gas concentration operate on a three shift or twenty-four hour basis. During each shift a different operator generally runs each gas analysis instrument. Thus, in a normal twenty-four hour day it is necessary to calibrate the instrument against the known sample and check it against two known standards three times, once for each eight hour shift. In case of power failures, other break downs or the like further calibration will be needed within each twenty-four hour day.

Generally the prior art apparatus for equilibrating an aqueous solution with a gas of a known composition has provided for relatively slow equilibration. One such instrument operates by introducing a gas of a known composition into a rotating sample tube whereby the surface area of the liquid being contacted with the gas is increased since the liquid is spread out against the sides of the tube as it rotates. Such an apparatus provides good equilibration but such equilibration will generally require about twenty to thirty minutes to time. Also, the apparatus must be re-used for each of the test samples which are to be prepared for checking the calibration of the instrument. Thus, with such an instrument it is necessary to equilibrate three samples with each equilibration taking about twenty to thirty minutes whereby about one hour of each eight hour shift is used up in preparing samples for standardizing the blood gas analyzer. Other available apparatus use such techniques as oscillation of the sample within a temperature controlled bath while a gas stream of known concentration is being flowed in contact with the liquid solution. In the oscillatory apparatus even slower attainment of equilibrium usually results.

The present invention is concerned with a gas equilibration apparatus which greatly cuts down time needed for preparing both a standard for calibrating a gas analyzer and the check or control solutions used to assure that the calibration of the instrument with the standard solution is correct.

SUMMARY OF THE INVENTION

In one sense the invention comprises apparatus for equilibrating a hydrophilic liquid with a gas. The apparatus comprises a gas vessel having therewithin a gas of a selectable composition at a pressure above ambient atmospheric pressure. Flow control means are provided for receiving flow from the vessel and controlling flow rate therefrom. A solution tube is provided having a hydrophilic liquid such as an aqueous liquid therewithin. Conduit means lead from the flow control means to the tube below a liquid level of the aqueous solution. Means are provided for causing the gas to be delivered within the aqueous solution below the liquid level as a plurality of bubbles. Preferably, the apparatus includes a heat conductive block having a cavity therewithin shaped to matingly hold the tube therewithin and means for adjusting the temperature of the block and thereby the temperature of the tube and the solution.

In another sense the invention comprises apparatus for simultaneously equilibrating a plurality of aqueous solutions with a plurality of gas compositions. The apparatus for simultaneous equilibration comprises a plurality of gas vessels each having therewithin a gas of a particular composition at a pressure above ambient atmospheric pressure. A plurality of flow control means are provided, one for receiving flow from each of the vessels and controlling the flow rate therefrom. A plurality of solution tubes are provided each holding a hydrophilic liquid, generally an aqueous solution, therewithin. A plurality of conduit means are provided one leading from each respective one of the flow control means to a respective one of the tube below a respective liquid level of the aqueous solution therewithin. Also, a plurality of means are provided for causing the gas to be delivered as bubbles within each respective aqueous solution below a respective liquid level thereof. The apparatus further preferably includes a heat conductive block having a plurality of cavities therewithin each shaped to matingly hold a respective one of the tubes therewithin and means for adjusting the temperature of the block and thereby the temperatures of the tubes and the solutions.

In yet another sense the invention comprises an improvement in an apparatus for equilibrating a hydrophilic liquid such as an aqueous solution with a gas composition which comprises a gas vessel having therewithin a gas of a selectable composition at a pressure above ambient atmospheric pressure, flow control means for receiving flow from said vessel and controlling the flow rate therefrom and a solution tube having an aqueous solution therewithin. The improvement provides extremely fast attainment of gas-solution equilibrium and comprises conduit means leading from the flow control means to the tube below a liquid level of the aqueous solution and means for causing the gas composition to be delivered within the aqueous solution within the liquid level as a plurality of bubbles.

In another sense yet the invention comprises a process for simultaneously equilibrating a plurality of hydrophilic liquid samples such as aqueous solutions each with one of a plurality of gas compositions. The process comprises positioning a plurality of solution tubes each having an open end and a closed end in mating fit within a respective one of a plurality of cavities formed within a heat conductive block with the open end of each tube positioned upwardly and a respective one of a plurality of aqueous solution in each of the tubes. The temperature of the solutions are adjusted to be substantially equal by controlling the temperature of the block to be a desired value. A respective one of the plurality of gas compositions is delivered below a respective liquid level of a respective aqueous solution within each respective one of said tubes in the form of bubbles.

It is an object of the present invention to provide apparatus and a process for equilibrating aqueous solutions with a gas.

It is a further object of the present invention to provide apparatus for simultaneously equilibrating a plurality of aqueous solutions with a gas in a minimal period of time.

It is a further object yet of the invention to provide an apparatus which reduces the calibration time for blood gas analyzers.

It is a further object still of the present invention to provide a compact apparatus which will quickly equilibrate an aqueous solution with a gas.

These and other objects of the invention are attained in using the apparatus and process as described below and its equivalents.

BRIEF DESCRIPTION OF THE DRAWINGS

The invention will be better understood by reference to the figures of the drawings wherein like numbers denote like parts throughout and wherein:

FIG. 1 illustrates in side section an apparatus in accordance with the present invention;

FIG. 2 illustrates a view taken along the line II—II of FIG. 1;

FIG. 3 illustrates in side elevation a heating block useful in the apparatus of the present invention;

FIG. 4 illustrates a view taken along the line IV—IV of FIG. 3;

FIG. 5 illustrates a view taken along line V—V of FIG. 3;

FIG. 6 illustrates a view taken along the line VI—VI of FIG. 5;

FIG. 7 illustrates a detail in a construction of apparatus useful in the practice of the present invention;

FIG. 8 illustrates a view taken along the line VIII—VIII of FIG. 7;

FIG. 9 illustrates an alternate embodiment of the view shown in FIG. 6 wherein the block includes a single cavity and a single cell;

FIG. 10 illustrates an improved cell in accordance with the present invention;

FIG. 11 illustrates a view taken along the line XI—XI of FIG. 10;

FIG. 12 illustrates a view taken along the line XII—XII of FIG. 10;

FIG. 13 illustrates a blown-up view of the area XIII—XIII of FIG. 10, in section;

FIG. 14 illustrates a blown-up view of a cylinder end with a handle extending therefrom useful in the practice of the present invention; and FIG. 15 illustrates a view taken along the line XV—XV of FIG. 14.

DETAILED DESCRIPTION OF THE PREFERRED EMBODIMENTS

The present invention is particularly concerned with an apparatus 10 shown in its entirety in FIGS. 1 and 2 for equilibrating a hydrophilic liquid which will not wet a hydrophobic surface (will not have a 90° contact angle therewith, as discussed, e.g., in Modern Colloids by Robert B. Dean, D. Van Nostrand Company, Inc., New York, 1948 at pages 62–66.) such as an aqueous solution, more generally a plurality of aqueous solutions 12, with a gas contained within one of a plurality of gas vessels 14. Each of the gas vessels 14 has therewithin a gas of a selectable composition at a pressure above ambient atmospheric pressure. Flow control means 16, in the embodiment illustrated in FIGS. 1 and 2 a plurality of flow control means 16 comprising a plurality of needle valves 18 each having knobs 20 and each leading to flow meters 22, which flow meters 22 generally comprise a tube 24 having a ball 26 suspended therein by the air flowing through the valve 18 each conduct gas via a plurality of lines 28, one to each of a plurality of cells 30, each of which in the embodiment illustrated comprises a sample tube 32. As will be noted, each of the plurality of lines 28 leads from the respective flow meter 22 to the tube 32 below a liquid level 34 of the aqueous solution 12. A hinged cover 35 is generally provided to assure non-contamination of the solution 12.

Means are also provided for causing the gas to be delivered within the aqueous solution while below the liquid level 34 as a plurality of fine bubbles. In the particular embodiment illustrated in FIG. 1 for example, the bubble delivering means comprises a plurality of membranes 36 each of which fits across a closed end 38 of a respective solution tube 32.

The solution tubes 32 fit within one of a plurality of cavities 40 formed within a heat conductive block 42. Thus, through adjustment of the temperature of the block 42 the temperature of each of the solutions 12 can be controlled to be substantially the same. Generally, the temperature of the gas passing through each of the respective plurality of lines 28 is equilibrated to be equal to that of the temperature of the block 42 as by passing the gas from each of the respective one of the plurality of lines 28 through a respective maze or contact path 44 and thence via a short conduit 46 to against the respective of the membranes 36.

As will be clear by reference to FIG. 1 each of the cavities 40 matingly holds a respective tube 32 therewithin. In contact with the block 42 and generally wrapped thereabout is a heater 48 for adjusting the temperature of the block and thereby the temperature of the tubes 32 and the solutions 12. Means are also provided for measuring the temperature of the block. In the embodiment illustrated these means comprise a thermocouple 50 or other temperature measuring device fitting within a wall 52 in the block 42. A pair of electric leads 54 from the thermocouple 50 leads generally to a bridge circuit 56 which has a meter 58 on which temperature can be read out either directly or as an electrical quantity such as voltage or the like which can be easily converted into an equivalent temperature. A temperature adjusting knob 60 is provided for controlling the heater 48 so that the temperature of the block 42 and thus of each of the solutions 12 can be controlled to a desired value. An on-off switch 62 is also provided in line between the heater 48 and a wall plug 64 to assure that the machine can be easily and completely turned off when not in operation. It is clear that the simple bridge 56 along with the meter 58, temperature adjusting knob 60 and thermocouple 50 can be replaced with a feedback network whereby the temperature adjusting knob 60 can be set to any desired temperature and the heater 48 will then be controlled thereby in a feedback network to adjust the temperature of the block 42 until the temperature set on the meter 48 by the knob 60 is attained.

The structure of the block 42 is shown in considerably greater detail in FIGS. 3, 4 and 5. As previously mentioned, the block 42 is generally made of a heat conducting material such as copper or the like. The three cavities 40 are provided within the block 42 and generally extend to adjacent a bottom end 66 of the block 42. Each of the cavities 40 has a compressible member 68 which serves as compressible sealing means for sealing the respective cavity 40 to a respective exterior of the respective tube 24 and providing a compression force to hold the tube 24 within the cavity 40. Generally, the compressible sealing means will simply comprise a compressible O-ring or the like made of generally a plastic or preferably an elastomeric material such as, for example, Viton E60(a copolymer of hexafluoropropylene and vinylidenefluoride) or the like.

FIG. 4 most particularly illustrates a plurality of contact paths 44 which as previously mentioned serve to equilibrate the temperature of the gas flowing from the flow control means 16 and more particularly from the flow meters 22 to the respective of the sample tubes 32. In the embodiment illustrated in FIG. 4 there are three contact paths 44 provided. Gas from a respective one of the plurality of lines 28 enters a respective one of the contact paths 44 at an entrance 70 thereto, passes through the mazelike contact path 44 and then exits the contact path 44 at an exit 72 from whence it flows via a respective one of the conduits 46 to below a closed end 38 of the respective one of the tubes 24 and more particularly against a bottom side of one of the plurality of membranes 36. The compressible members 58, meanwhile, assures that the gas cannot escape around the respective one of the tubes 32 and up through the cavity 40 to the surrounding atmosphere. Thus, the only escape path for gas introduced via the conduit 46 is through the respective membrane 36. This assures the build up of enough pressure below the respective one of the membranes 36 to assure gas flow will occur therethrough into the respective aqueous solution 12.

Turning now most particularly to the membranes 36 which comprise the preferred bubble delivering means of the invention it will be noted that each of these membranes comprise a porous member having a hydrophobic surface and that said porous member forms the bottom or closed end 38 of the respective one of the solution tubes 32. Each of the membranes 36 is impervious to flow of the aqueous solution therethrough when the solution tube 32 is filled with the aqueous solution 12 and is permeable to flow of the gas composition upwardly therethrough. Generally, each of the membranes 36 will have microscopic (capillary) paths therethrough and since the surface of the membranes 36 is hydrophobic the solution will not wet the microscopic capillary paths and thus will be held from flowing therethrough. On the other hand, gas will not be held up significantly by the microscopic or capillary paths and will simply pass upwardly therethrough against the head created by the respective of the solutions 12. Because of the relatively small size of the capillaries leading through the membranes 36 the size of the bubbles introduced into the bottom of each of the solution tubes 32 will be extremely fine thus leading to very efficient surface to liquid contact as well as agitation whereby equilibrium will be extremely rapidly attained between the gas composition and the respective one of the solutions 12 through which it is being passed. More specifically, such equilibration has been found to take no more than about three to four minutes for a 10 cc. sample of aqueous solution 12. This is considerably less than the twenty to thirty minutes needed for equilibration of an aqueous solution using the fastest of the prior art apparatus for accomplishing this.

Referring now once again to FIG. 1 it will be apparent that each of the plurality of gas vessels 14 delivers the gas therefrom to a pressure regulator 74 before that gas is allowed to flow to a needle valve 18. Typically, the pressure within the gas vessel 14 might be several hundred psi while the pressure regulator 74 might provide for a pressure of no more than five psi. In this manner, the needle valves 18 are each operating with a constant upstream gas pressure head until the respective gas vessel 14 empties to below the pressure head to which the pressure regulator 74 is set. This assures that flow rates through the respective flow control means 16 are generally constant independent of the pressure within the respective bottles 14 so long as that pressure exceeds the setting of the pressure regulator 74.

Turning now most particularly to FIG. 6 it will be seen that the block 42 will generally be set within an insulating container 76 to assure proper and accurate temperature control.

FIGS. 7 and 8 illustrate a plate 78 which is made to abut the bottom 66 of the block 42 and to seal the three contact paths 44 each from each other. At a bottom side 80 of the plate 78 there are a plurality of nipples 82 to which the lines 28 are attachable. Also, the plate 78 has a hole 84 central therethrough which forms a continuation of the well 52.

Turning now to FIG. 9 there is illustrated an alternate embodiment of the invention wherein the block 42 has therein a single cavity 40 with a single aqueous solution 12 within a single solution tube 32. In this embodiment, the plate 78 which fits against the bottom 66 of the block 42 has a single nipple 82 extending therefrom which connects with a single line 28 from a single flow meter 22. The block 42 has a single maze or contact path 44 therewithin adjacent the bottom 66 thereof whereby the gas which flows through the line 28 is brought to the temperature of the block 42 before passing via a single conduit 46 to the bottom of the membrane 36 and then through the membrane and through the solution 12 therewithin. In a like manner to the embodiment shown in great detail in for example FIG. 6, a compressible member 68 is provided to form a gas tight fit between the solution tube 32 and the cavity 40. As will be noted, in the embodiment shown in FIG. 9 the thermocouple 50 enters the block 42 via a well 52 from a top 86 of the block 42 rather than from the bottom 66 thereof as in the embodiment illustrated most clearly in FIG. 6.

Turning now most particularly to FIGS. 10–13 there is illustrated therein a cell 30 in accordance with present invention which comprises the sample tube 32. It should generally be noted that the sample tube 32 is generally tapered from an upper end 88 thereof to a lower end 90 thereof so as to be generally frustoconical in shape whereby when it is placed in the respective one of the cavities 40 it can easily be inserted because of a relatively large fit at the top of a likewise tapered cavity 40. The tube 32 generally includes support means such as a support structure 92, in the embodiment illustrated a cross-shaped support structure 92 which is integrally and unitarily formed with the tube 32 interiorly of the tube 32 and abutting of the membrane 36 to prevent the membrane 36 from tearing. Generally the tube 32 will comprise a first polymeric material which is generally of a rigid nature. Any polymeric material may be used which will have the desired stiffness and be non-reactive to the aqueous solution contained therein and the gas bubbled through the respective one of the membranes 36. For example the tube 32 can be made of polyethylene, polypropylene, or any number of plastic materials having structural integrity (and referred to herein for convenience as rigid). Alternatively, the tube 32 can be made of any number of rigid (having structural integrity) elastomeric materials.

Generally, the membrane 36 will comprise a second polymeric material which may conceivably be chemically similar to or the same as the first polymeric material. The only requirement for the second polymeric material is that it be inert to the aqueous solution which would be held in contact therewith and to the gas which is to pass therethrough. Of course as previously mentioned the member 36 must provide a hydrophobic surface. Thus, the member 36 can be formed of a second polymeric material which is plastic in nature or elastomeric in nature so long as it has the necessary porosity to allow gas flow upwardly therethrough and the necessary hydrophobic character to prevent the aqueous solution 12 from flowing therethrough. For example, polyethylene, polypropylene and other polymeric membranes are particularly suitable as the membrane 36.

Turning now most particularly to FIG. 13 there is illustrated therein means for detachably attaching the membrane to the tube to form the lower closed end 38 of the tube 32. The particular detachable attaching means shown comprises a ring 94 which may itself be made of a rigid polymeric material or alternatively be made of metal and which fits matingly within a sleeve 96 which extends longitudinally from the closed end 38 of the tube 32 coaxially therewith. The ring 94 forms a mating fit within the sleeve 96 with the membrane 36 pressed therebetween. Generally, the tube 32 is made of a material that preferably is formable into said tube 32 by injection molding techniques so as to reduce the cost and time of production thereof.

In an apparatus 10 which includes a plurality of the tubes 32, the tubes 32 are preferably each coded as for example by making each of the tubes 32 a different color so that each of the tubes 32 when placed in a correspondingly coded one of the cavities 40 will receive a gas composition which originally came from a particularly known and coded one of the gas vessel 14. Thus for example one of the tubes 12 could conceivably be red in color and this tube 12 would then be aligned, for example, next to a red dot and would receive flow from a cylinder 14 which was coded to a red color. Alternatively to the use of color codes, one can of course use upraised bumps, markings, numerals or the like.

Turning now particularly to FIGS. 1, 2, 14 and 15 the structure of the gas vessels 14 and the interrelationship with the apparatus 10 as a whole will be explained in some detail. It is clear that each of the cylinders 14 is closed at a first end 98 thereof and has valve means such as a ball valve 100 adjacent a second end 102 thereof. The second end 102 of the cylinder 14 has extending longitudinally therefrom a threaded neck 104 of smaller diameter than the cylinder 14. The first end 98 of the cylinder 14 has extending longitudinally therefrom handle means, in the embodiment illustrated a handle 106, the handle 106 not extending radially significantly beyond the diameter of the cylinder 14. As will be most clear by reference to FIGS. 1 and 14 the handle 106 is preferably separately formed from the cylinder 14 and preferably includes fastening means 108 including a disc 110 extending to the diameter of the cylinder 14 and sleeve means such as a sleeve 112 which grippingly extends along an exterior surface 114 of the cylinder 14 a short distance in the direction of the second end 102 thereof. Thus, it is clear that the sleeve 112 fits tightly and grippingly about the exterior surface 114 of the cylinder 14 adjacent the first end 98 thereof. It is further clear that the handle 106 and the fastening means 108 which includes the disc 110 and the sleeve 112 generally comprises a unitary polymeric structure. It is preferred that the unitary polymeric structure comprise a rigid plastic or a rigid elastomer with the term rigid used again to connote structural integrity. As will be noted by reference to FIGS. 1 and 14 the handle 106 generally extends from the first end 98 of the cylinder 14 no more than at most one-third the length of the cylinder 14 and more generally no more than at most one-fifth the length thereof.

It should be noted that the ball valve 100 will generally be operated through the threaded neck 104 in a conventional manner.

Adverting again to FIGS. 1, 2, 14 and 15 it will be noted that a frame 116 of the apparatus 10 will generally include extending therefrom threaded fitting means such as the threaded female fittings 118 illustrated in FIG. 1. It is clear that the threaded fitting 118 is positioned to receive the threaded neck 104 of the cylinder 14 and the means that operate the ball valve 104 extend through the threaded neck 104 and into contact with the ball valve 100. As will further be noted most particularly by reference to FIGS. 1 and 14, there is formed within the frame 116 a cylindrical bore portion 120. In the case of apparatus which includes multiple cylinders 14 there will be a plurality of bores 120. An internal diameter of the cylindrical bore portion 120 is made substantially equal to and slightly greater than an external diameter of the cylinder 14. At the same time the threaded fitting 118 is positioned as by support means 122 and the pressure regulator 74 adjacent a first end 124 of the cylindrical bore portion 120 and generally along the axis of the cylindrical bore portion 120. In this manner, the cylinder 14 is insertable in the cylindrical bore portion 120 to align the threaded neck 104 with the threaded fitting 118 and the handle 106 is turnable to cause the threaded neck 104 to turn therewith and thread with the threaded fitting 118. As will further be noted by reference to FIGS. 1, 14 and 15 a second end 126 of the cylindrical bore portion 120 preferably includes an annulus 128 of a size and shape to accommodate the sleeve 112 of the fastening means 108. The handle 106 is generally restricted in size radially so as not to extend beyond the annulus 128. Thus it is clear that the bore 120 aligns the cylinder 14 for fast and proper threading between the neck 104 and the threaded fitting 118.

Each of the cylinders 14 along with the respective fastening means 108 and handle 106 forms a cylinder assembly 130. Each of the cylinder assemblies 130 in those apparatus 10 which include a plurality of cylinder assemblies 130 is generally coded to indicated into which respective one of said cylindrical bore portions 120 the particular cylinder assembly 130 is to be inserted. For example the respective handle 106, fastening means 108, and/or cylinder 14 can be color coded, can be numbered, or can otherwise be coded to correspond with coding which appears adjacent a respective one of the cylindrical bore portions 120.

Turning most particularly to FIGS. 1 and 14 it will be noted that a door 132 is generally provided as part of the frame 116, which door 132 is closable when the respective cylinder assemblies 130 are fully inserted within the respective of the cylindrical bore portions 120 and the respective of the threaded necks 104 are threaded within the respective of the threaded fittings 118. Thus, through use of the handle 106 attached to the back of the cylinder 14 one can make use of the alignment provided by the cylindrical bore portion 120 thus acquiring a blind or sightless fit of the neck 104 into threaded relationship with the threaded fitting 118 while at the same time allowing the door 132 to be closed fully thus providing no projecting parts from the frame 116 of the apparatus 10. This is clearly advantageous since the cylinders 114 are thus prevented from being damaged by their being completely enclosed within the respective of the cylindrical bore portions 120. In the absence of a handle such as 106 attached to the respective of the cylinders 14, the first end 98 of the respective cylinders 14 would potentially extend outwardly beyond the frame 116 thus exposing the cylinder 14 to possible damage and providing projecting parts on which an operator could be harmed.

While the invention has been described in connection with specific embodiments thereof, it will be understood that it is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. Apparatus for equilibrating a hydrophilic liquid such as an aqueous solution with a gas, comprising:
   a gas vessel having therewithin a gas of a selectable composition at a pressure above ambient atmospheric pressure;
   flow control means receiving flow from said vessel and controlling a flow rate therefrom;
   a removable solution tube having a hydrophilic liquid therewithin;
   a heat conductive block having a cavity therewithin sealingly matingly holding said removable tube therewithin;
   conduit means leading from said flow control means to said tube below a liquid level of said hydrophilic liquid; and
   means for causing said gas to be delivered within said hydrophilic liquid below said liquid level as a plurality of bubbles.

2. Apparatus as in claim 1, wherein said bubble delivery means comprises a porous member having a hydrophobic surface forming a bottom of said tube, said member being impervious to flow of said liquid therethrough when said tube if filled therewith and being permeable to flow of said gas composition upwardly therethrough.

3. Apparatus as in claim 2, including:
   means for adjusting the temperature of said block and thereby the temperature of said tube and said liquid.

4. Apparatus as in claim 3, including:
   means for equilibrating the temperature of said gas with the temperature of said block.

5. Apparatus as in claim 4, including:
   means for measuring the temperature of said block.

6. Apparatus as in claim 3, wherein said cavity sealingly matingly removably holds said tube via compressible sealing means which seal said cavity to an exterior of said tube and provide a compression force to hold said tube within said cavity.

7. Apparatus as in claim 2, including, intermediate said vessel and said flow control means:
   pressure regulator means for regulating a pressure of said gas exiting therefrom to a selected valve.

8. Apparatus for simultaneously equilibrating a plurality of hydrophilic liquids such as aqueous solutions with a plurality of gas compositions, comprising:
   a plurality of gas vessels each having therewithin a gas of a particular composition at a pressure above atmospheric pressure;
   a plurality of flow control means, one for receiving flow from each of said vessels and controlling the flow rate therefrom;
   a plurality of removable solution tubes, each holding a hydrophilic liquid therewithin;
   a heat conductive block having a plurality of cavities therewithin, each sealingly matingly holding a respective one of said tubes removably therewithin;
   a plurality of conduit means, one leading from each respective one of said tubes below a respective liquid level of the liquid therewithin; and
   a plurality of means for causing said gas to be delivered as bubbles within each respective liquid below a respective liquid level thereof.

9. Apparatus as in claim 8, including:
   means for adjusting the temperature of said block and thereby the temperature of said tubes and said liquids.

10. Apparatus as in claim 9, including:
    means for equilibrating the temperature of each of said gases with the temperature of said block.

11. Apparatus as in claim 10, including:
    means for measuring the temperature of said block.

12. Apparatus as in claim 10, wherein said bubble delivery means each comprise a porous member having a hydrophobic surface forming a bottom of a respective one of said tubes, said members being impervious to flow of said liquid therethrough when said tubes are filled therewith and being permeable to flow of said gases upwardly therethrough.

13. Apparatus as in claim 12, wherein said cavities sealingly matingly removably hold said tubes via a plurality of compressible sealing means each sealing a respective one of said cavities to an exterior of a respective one of said tubes and providing a compression force to hold said respective one of said tubes within said respective one of said cavities.

14. Apparatus as in claim 10, including:
    a plurality of pressure regulator means, one intermediate each respective one of said vessels and a respective one of said flow control means, for regulating a pressure of a respective one of said gases exiting said respective pressure regulator means to a selected value.

15. In an apparatus for equilibrating an aqueous solution with a gas composition which comprises a gas vessel having therewithin a gas of a selectable composition at a pressure above ambient atmospheric pressure, flow control means for receiving flow from said vessel and controlling a flow rate therefrom and a removable solution tube having an aqueous solution therewithin, an improvement which provides extremely fast attainment of gas-solution equilibrium, comprising:
a heat conductive block having a cavity therewithin sealingly matingly holding said tube removably therewithin;
conduit means leading from said flow control means to said tube below a liquid level of said aqueous solution; and
means for causing said gas composition to be delivered within said aqueous solution below said liquid level as a plurality of bubbles.

16. An improved apparatus as in claim 15, wherein said bubble delivery means comprises a porous member having a hydrophobic surface forming a bottom of said tube, said member being impervious to flow of said solution therethrough when said tube is filled therewith and being permeable to flow of said gas composition upwardly therethrough.

17. An improved apparatus as in claim 16, including:
means for adjusting the temperature of said block and thereby the temperature of said tube and said solution.

18. An improved apparatus as in claim 17, including:
means for equilibrating the temperature of said gas with the temperature of said block.

19. An improved apparatus as in claim 18, including:
means for measuring the temperature of said block.

20. An improved apparatus as in claim 16, wherein said cavity sealingly matingly removably holds said tube via compressible sealing means which seal said cavity to an exterior of said tube and provide a compression force to hold said tube within said cavity.

21. An improved apparatus as in claim 20, including, intermediate said vessel and said flow control means:
pressure regulator means for regulating a pressure of said gas exiting therefrom to a selected valve.

22. A process for simultaneously equilibrating a plurality of aqueous solutions each with one of a plurality of gas compositions, comprising:
positioning a plurality of solution tubes each having an open end and a closed end in sealing mating fit within a respective one of a plurality of cavities formed within a heat conductive block with the open end thereof upwardly and a respective one of a plurality of aqueous solutions in each of said tubes;
adjusting the temperature of said solutions to be substantially equal by controlling the temperature of said block to a desired value; and
delivering a respective one of said plurality of gas compositions below a respective liquid level of a respective aqueous solution within each respective one of said tubes in the form of bubbles.

23. A process as in claim 22, wherein said tubes each include closing the closed end thereof of a porous member having a hydrophobic surface to prevent flow of said respective aqueous solution therethrough and said delivery step comprises introducing a respective one of said plurality of gas compositions against a bottom side of each respective one of said cavities at a sufficient pressure to force said respective one of said compositions to flow through said respective one of said members and form a plurality of bubbles within each respective one of said tubes adjacent a respective closed end thereof.

* * * * *